(12) United States Patent
Olsen

(10) Patent No.: US 8,676,339 B1
(45) Date of Patent: Mar. 18, 2014

(54) SURFACE WARMING DIATHERMY APPARATUS AND METHOD

(76) Inventor: Richard G. Olsen, Pensacola, FL (US)

(*) Notice: Subject to any disclaimer, the term of this patent is extended or adjusted under 35 U.S.C. 154(b) by 437 days.

(21) Appl. No.: 13/136,130

(22) Filed: Jul. 25, 2011

(51) Int. Cl.
*A61F 2/00* (2006.01)

(52) U.S. Cl.
USPC .................................................. 607/101

(58) Field of Classification Search
USPC .......................................... 607/96, 100, 101
See application file for complete search history.

(56) References Cited

U.S. PATENT DOCUMENTS

| 6,094,599 A | 7/2000 | Bingham et al. |
| 6,735,481 B1 | 5/2004 | Bingham et al. |
| 2004/0044386 A1 * | 3/2004 | Beens et al. .................. 607/101 |

* cited by examiner

*Primary Examiner* — Linda Dvorak
*Assistant Examiner* — Jared W Pike
(74) *Attorney, Agent, or Firm* — J. Nevin Shaffer, Jr.

(57) ABSTRACT

A surface warming diathermy apparatus and method includes an applicator with a first chamber and a second chamber where the first chamber contains a dielectric solution. A primary coil is wrapped around the applicator beginning with the first chamber. A secondary coil is wrapped around the applicator also beginning with the first chamber and a RF energy source connected with the primary coil. The apparatus is tuned to a near resonant state by means of a variable high-voltage capacitor connected to each end of the secondary coil.

20 Claims, 1 Drawing Sheet

SURFACE WARMING DIATHERMY APPARATUS AND METHOD

FIELD OF THE INVENTION

This invention relates to a surface warming diathermy apparatus and method. In particular, in accordance with one embodiment, the invention relates to a surface warming diathermy apparatus including an applicator with a first chamber and a second chamber where the first chamber contains a dielectric solution. A primary coil is wrapped around the applicator beginning with the first chamber. A secondary coil is wrapped around the applicator also beginning with the first chamber and a RF energy source connected with the primary coil.

BACKGROUND OF THE INVENTION

Within the area of Dermatology, a need for a very safe, easy to use, energy efficient skin warmer exists. Applicant has created devices, among others, such as an elastic wire configuration (U.S. Pat. No. 6,735,481) and a garment for enclosing a body part using a RF diathermy coil (U.S. Pat. No. 6,094,599). These inventions solved existing problems relating to wound healing and stimulation of injuries to enhance healing, for example only, but are not suitable as disclosed for use in this area of Dermatology where the body part can not be wrapped or the use is for multiple and or extremely sensitive areas.

With this as background, Applicant has determined that what is needed is a device that is easy to operate with a high degree of nearly instantaneous ability to control the level of heating applied to the skin. Further, it is required that the device be able to produce a high degree of skin warming while minimizing the possibility of injurious burns. Further, it is a particular need for a warming device that can be safely used to provide gentle warming for facial areas.

It, therefore, is an object of this invention to provide a surface warming device for the application of controlled heating to selected areas. It is a further object of the invention to provide an easy to use, efficient and safe warming device. It is a still further object to provide a device that produces a high degree of skin warming safely and in a controlled manner and that may be safely used on sensitive areas of the body, including, but not limited to the face.

SUMMARY OF THE INVENTION

Accordingly, the surface warming diathermy apparatus of the present invention, according to one embodiment includes an applicator with a first chamber and a second chamber where the first chamber contains a dielectric solution. A primary coil is wrapped around the applicator beginning with the first chamber. A secondary coil is wrapped around the applicator also beginning with the first chamber and a RF energy source is connected with the primary coil such that the RF ground lead is connected to the beginning of the primary coil.

As used herein, terms are given their ordinary meaning and are understood to include that meaning as used in conjunction with the description and figures set forth herein.

In one aspect, the dielectric solution is water, such as plain drinking water, and in another aspect the dielectric solution is pure water.

In a further aspect, the primary coil is a two turn coil and the secondary coil is a seven turn coil. In one aspect of the invention, approximately two wraps of the seven turn secondary coil are around the second chamber. In another aspect, the primary coil starts near the termination of the seven turn secondary coil. In a further aspect, the two turn primary coil starts one half turn before the start of the seven turn secondary coil. In another aspect, the secondary coil begins and ends on the same side of the applicator.

In one aspect of the invention, a tuner is connected with the secondary coil and in another aspect the tuner is a variable high voltage capacitor connected in parallel across the secondary coil.

In a further aspect, the primary coil and the secondary coil include insulation and the insulation on the secondary coil is relatively thinner in some locations. In one aspect, the insulation is thinner on the secondary coil in the area adjacent the second chamber such as at the tip of the second chamber.

According to another embodiment of the invention, a surface warming diathermy apparatus includes an applicator with a first chamber and a second chamber where the first chamber contains a dielectric solution. A seven turn secondary coil is wrapped around the applicator beginning with the first chamber. A two turn primary coil is wrapped around the applicator also beginning with the first chamber. A RF energy source is connected with the primary coil. A tuner is connected with the secondary coil and insulation is provided on the primary coil and the secondary coil where the insulation is thinner on the primary coil in the area adjacent the second chamber.

In one aspect of this invention, approximately two wraps of the seven turn secondary coil are around the empty second chamber. In another aspect, the two turn primary coil starts one half turn after the beginning of the seven turn secondary coil.

In another aspect, the tuner is a variable high voltage capacitor. In a further aspect, the secondary coil begins and ends on the same side of the applicator.

According to another embodiment of the invention, a method of surface warming diathermy consists of the steps:

a. providing an applicator with a first chamber and a second chamber where the first chamber contains a dielectric solution and the second chamber is virtually empty or filled with a dry low density foam like material; a primary coil wrapped around the applicator beginning with the first chamber; and a secondary coil wrapped around the applicator beginning with the first chamber; and b. connecting a RF energy source with the primary coil such that the RF ground lead connects to the beginning of the primary coil.

In another aspect, the method includes the step of holding the applicator next to the surface of skin so as to cause the skin to warm. In a further aspect, the method includes the step of connecting a tuner with the secondary coil such that the high heat tuned circuit comprised by the seven turn coil and the tuner capacitor is in a near resonant condition before the applicator is held close to the skin, body capacitance is added to the circuit and resonance occurs.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
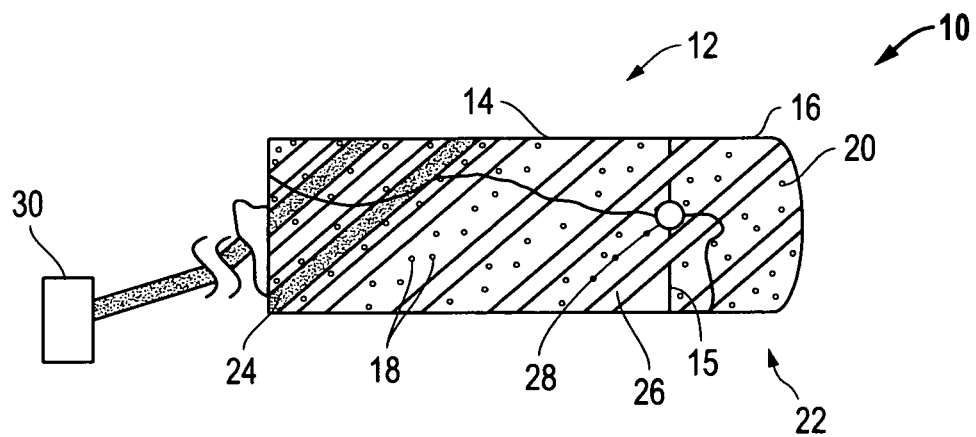
FIG. 1 is a side view of the surface warming diathermy apparatus according to one embodiment.
Figure 2:
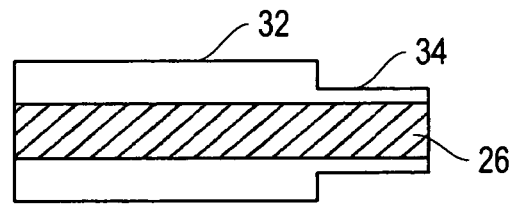
FIG. 2 is a side section view of a section of coil with insulation.
Figure 3:
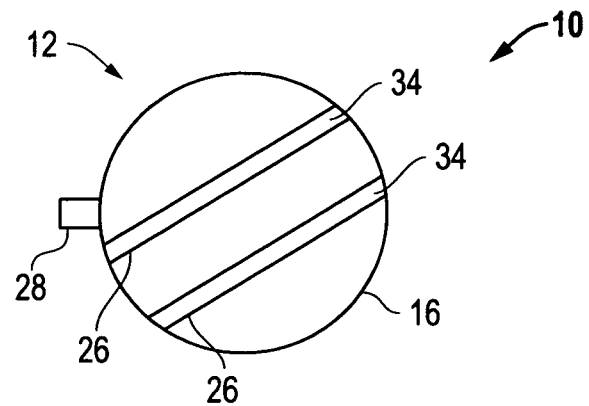
FIG. 3 is a front view of the invention of FIG. 1.

The preferred embodiment of the present invention is illustrated by way of example in FIGS. 1-3. With specific reference to FIG. 1, a surface warming diathermy apparatus 10 includes an applicator 12. As used herein, the term "applicator" is given its ordinary meaning for a device for applying something. In this instance the thing being "applied" is heat producing RF energy from one end of the applicator as will be explained herein.

Applicator 12 includes a first chamber 14 and a second chamber 16. Again, as used herein, "chamber" is given its common and ordinary meaning for a separate and discrete area within a single device. Thus, the applicator 12 is preferably a single device with two separate sections.

First chamber 14 is conformed to contain a dielectric solution 18. Dielectric solution 18 may be any dielectric solution now known or hereafter developed including but not limited to saline solutions, water, drinking water and pure water. According to a preferred embodiment, as will be described more fully hereafter, pure water is used as the dielectric solution 18.

Second chamber 16 is part of applicator 12 and connected with or is located in close proximity to, first chamber 14. Second chamber 16 is, in a preferred embodiment, empty and contains no dielectric 18. Second chamber 16 may include a gas 20, such as air, for example only and not by way of limitation.

Second chamber 16 is preferably made from an elastic material that can be deformed but which, when released from stress or pressure, returns to its starting or resting position 22 as shown in FIG. 1. Any elastic material, such as plastic, now known or hereafter developed is suitable for the purposes of the invention. First chamber 14 may be made of the same material.

This "elastic" feature of second chamber 16 enables the applicator 12 to be pressed to the surface of the user's skin, for example only, and to deform to conform to the contours of the body at that location. For example, it deforms to the contour of the user's chin or forehead by expanding and deforming when pressed into place.

Still referring to FIG. 1, primary coil 24 is wrapped around applicator 12 beginning with the first chamber 14. Secondary coil 26 is wrapped around applicator 12 also beginning with the first chamber 14. Preferably primary coil 24 is a two turn coil and preferably secondary coil 26 is a seven turn coil as illustrated. Also, preferably, approximately two wraps of the seven turn secondary coil 26 are around the second chamber 16 and the windings begin and end on the same side of the applicator 12, as shown. Further, preferably, primary coil 24 starts one-half turn after the start of the seven turn secondary coil 26. Both windings are right hand wound.

The two turn primary coil 24 serves as the impedance matching "primary winding" of a common RF transformer circuit. For the given geometry, it has been empirically determined that a near perfect 50-Ohm match for this circuit, at 27.12 MHz, will occur when approximately fifty percent of turn one and twenty-five percent of turn two are routed very close to the seven turn secondary coil 26, while other portions of the two turn primary coil 24 are located equidistant between the windings of the seven turn secondary coil 26.

Still referring to FIG. 1, a tuner 28 is provided. Preferably tuner 28 is a variable high voltage capacitor. Tuner 28 is connected across the seven turn secondary coil 26 to bring the applicator 12 to near a resonate state. Applicant has discovered that for similarly sized people the surface warming diathermy apparatus 10 can be successfully operated with a fixed capacitor provided that it has a substantial high voltage rating.

FIG. 1 also illustrates RF energy source 30 connected, in a preferred embodiment in parallel, with primary coil 24 with the ground connector connected to the beginning of the primary winding as illustrated. Preferably RF energy source 30 operates at 27.12 MHz, with at least thirty watts of power capability and a fifty Ohm output impedance.

Referring now to FIG. 2, a section of secondary coil 26 is illustrated. Preferably, both primary coil 24 and secondary coil 26 are covered with insulation 32. Insulation 32 may be any type of electrical insulation now known or hereafter developed. Importantly, Applicant has determined that the most effective use of the surface warming diathermy apparatus 10 occurs when a section of the secondary coil 26 is thinner in some sections than in others. Preferably the thin section 34 occurs in the portion of secondary coil 26 consisting of at least some of the two turns covering the second chamber 16. It is this area of surface warming diathermy apparatus 10 that is brought next to or pressed into contact with the skin surface of the user. Applicant has determined that a thickness of two to three sheets of plastic, such as for example only common kitchen wrap, is sufficient to insulate the secondary coil 26 but provides extraordinarily and unexpectedly good warming.

Referring now to FIG. 3 an end view of the surface warming diathermy apparatus 10 is shown with secondary coil 26 with approximately two wraps around the second chamber 16. Also, preferably, thin section 34 of insulation 30 covers the secondary coil 26 in at least some of this area.

In operation, a user connects the applicator 12 to RF energy source 30. A fifty Ohm cable would serve the purpose. Then the RF energy source 30 is energized and the surface warming diathermy apparatus 10 second chamber 16 is pressed against the skin, touching the skin with the portion of the seven turn secondary coil 26 covering the second chamber 16. The tuner 28 is then adjusted until a desired maximum skin heating is obtained. Surface warming diathermy apparatus 10 may include a panel meter or lighted bar graph or some other indicator (not shown) of the relative amount of RF energy being transmitted to the skin if desired. A less cumbersome and more responsive indicator is for the user simply to move the applicator 12 to a different location when the heat becomes uncomfortable or remove it from contact with the skin altogether. Moving the applicator in a systematic manner to nearby locations is an effective way to raise the temperature of a larger and larger region of surface tissue should this be desired.

By way of further explanation, the resonant coil, shared energy RF skin heating invention described herein may obviously be made in different sizes. That is, the size of applicator 12 may be reduced as the RF frequencies are increased. In any event, the "Hot end", second chamber 16, of the device comprising again approximately the last two coil windings of the seven turn secondary coil 26 wound over the empty second chamber 16 is an important element of the invention. That is, Applicant has found that an applicator 12 without the empty second chamber 16 is significantly less effective although functional. Unexpectedly better warming results were achieved, however, by the combination of the first chamber 14 with the dielectric solution 18 coupled to the empty (except for air) second chamber 16. That is, the presence of a resonance producing, coil-wound bolus of water that is not associated with the "Hot" end of the device is another key feature of the invention.

Applicant has determined that the coil wound, high dielectric portion, first chamber 14, of the two chamber applicator 12 serves as an RF energy storage element (in microwave terms, a CAVITY) for the power transmitted from the RF energy source 30. This energy storage element, during resonance conditions, effectively shares its stored energy with the "Hot" end, second chamber 16, of the applicator 12 and comprises the "shared energy" nature of the invention. The use of pure water, Applicant has determined, considerably sharpens the resonance peak (thereby increasing the level of the energy stored) compared to prior art resonant coil RF warming systems where a (lossy dielectric) human limb occupied the coil interior. Again, pure water is not the only material that is acceptable to occupy the high dielectric portion, first chamber 14, as any high dielectric material with a low "loss tangent" could be used.

A key and unique feature of the warmer of sensitive and delicate skin tissue of the present invention is that RF energy historically called "evanescent wave energy" is used in conjunction with a circuit common in radio communications electronics. "Evanescence" is the characteristics of disappearing like a vapor. These energy waves are typically called leakage or stray irradiation. Leakage energy from an improperly closed microwave oven door is an example. These weaves are usually of low amplitude and exist very close to an energized conductor and they die or drop off quickly with distance from the conductor.

Applicant has determined that what makes these typically low-energy content waves useful for warming skin is the existence of localized regions of high voltage in a parallel connection of an inductor (coil) and a capacitor, known as a tank circuit, at resonance, that is appropriately energized. In the present preferred embodiment of the invention, Applicant has determined that about 30 watts of RF power can produce more than 2 kilovolts across the tuning capacitor at the peak of resonance. At this point, the wire connected with the "hot" end of the capacitor is an emitter of evanescent energy; at resonance, there is sufficient voltage very near the wire to produce a usable amount of prompt heating in a limited amount of tissue. One unexpected result and very beneficial feature of this scheme is that significant heating only occurs at the peak of resonance and resonance only occurs, Applicant has determined, as the applicator is brought close to the skin.

It should be understood that the addition of coil windings that are not coupled to the water bolus and that are located away from the impedance matching primary winding produce the opportunity to couple very high RF potentials to the skin. "Hot" end coil windings could easily be envisioned, perhaps, as serpentine, flattened insulated conductors with more of a planar geometry. All that is required in the operation of the invention is that a relatively sharp resonance be achieved as the "hot" end, second chamber 16, is pressed against the skin. This couples energy to the lossy dielectric capacitance of human skin, which coupling produces the required fine tuning to resonance. By way of further explanation, the sharpness of the apparatus' resonance characteristics allow for inherently safe operation, by only delivering RF energy to the skin as resonance is achieved by contact. As skin contact is lost, so is the coupled RF energy deposition. Thus, when the user feels the area of the skin is getting too warm, simply removing the applicator 12 from contact stops the warming. Further, the applicator 12 itself is not warm. This safety feature can be further enhanced through the use of an RF energy source 30 that has the ability to transmit power only when a load impedance is near fifty ohms such as the previously available Selicor, Inc. Model A100 Short Wave Diathermy Unit. With such an energy source, there is redundancy in the ability to quickly stop the skin warming process.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. A surface warming diathermy apparatus comprising:
   a. an applicator with a first chamber and a second chamber wherein said first chamber contains a dielectric solution;
   b. a primary coil wrapped around said applicator beginning with said first chamber;
   c. a secondary coil wrapped around said applicator also beginning with said first chamber; and
   d. a RF energy source connected with said primary coil.

2. The apparatus of claim 1 wherein said dielectric solution is water.

3. The apparatus of claim 1 wherein said dielectric solution is pure water.

4. The apparatus of claim 1 wherein said primary coil is a two turn coil and said secondary coil is a seven turn coil.

5. The apparatus of claim 4 wherein approximately two wraps of said seven turn secondary coil are around said second chamber.

6. The apparatus of claim 4 wherein said primary coil starts between the seven turns of the secondary coil.

7. The apparatus of claim 6 wherein said primary coil starts approximately one-half turn after the start of the seven turn secondary coil.

8. The apparatus of claim 4 wherein said secondary coil begins and ends on the same side of said applicator.

9. The apparatus of claim 1 further including a tuner connected with said secondary coil.

10. The apparatus of claim 9 wherein said tuner is a variable high voltage capacitor connected in parallel across said secondary coil.

11. The apparatus of claim 1 wherein said primary coil and said secondary coil include insulation and wherein the insulation on said primary coil is relatively thinner in some locations.

12. The apparatus of claim 11 wherein said insulation is thinner on said secondary coil in the area adjacent said second chamber.

13. A surface warming diathermy apparatus comprising:
   a. an applicator with a first chamber and a second chamber wherein said first chamber contains a dielectric solution;
   b. a two turn primary coil wrapped around said applicator beginning with said first chamber;
   c. a seven turn secondary coil wrapped around said applicator also beginning with said first chamber;
   d. a RF energy source connected with said primary coil;
   e. a tuner connected with said secondary coil; and
   f. insulation on said primary coil and said secondary coil wherein said insulation is thinner on said secondary coil in the area adjacent said second chamber.

14. The apparatus of claim 13 wherein approximately two wraps of said seven turn secondary coil are around said second chamber.

15. The apparatus of claim 13 wherein said two turn primary coil starts approximately one half turn after the beginning of the seven turn secondary coil.

16. The apparatus of claim 13 wherein said tuner is a variable high voltage capacitor.

17. The apparatus of claim 13 wherein said secondary coil begins and ends on the same side of said applicator.

18. A method of surface warming diathermy comprising:
   a. providing an applicator with a first chamber and a second chamber wherein said first chamber contains a dielectric solution; a primary coil wrapped around said applicator beginning with said first chamber; and a secondary coil wrapped around said applicator also beginning with said first chamber; and
   b. connecting a RF energy source with said primary coil.

19. The method of claim 18 further including holding said applicator next to the surface of skin so as to cause the skin to warm.

20. The method of claim 18 further including connecting a tuner with said secondary coil.

\* \* \* \* \*